United States Patent
Bianco

(10) Patent No.: US 10,426,581 B2
(45) Date of Patent: Oct. 1, 2019

(54) MODULAR SYSTEM FOR THE REALIZATION OF ORTHODONTIC GYPSUM MODELS

(71) Applicant: ORTOLAB POMPEI S.R.L., Pompei (IT)

(72) Inventor: Aniello Bianco, Scafati (IT)

(73) Assignee: Ortolab Pompei S.R.L., Pompei (IT)

( * ) Notice: Subject to any disclaimer, the term of this patent is extended or adjusted under 35 U.S.C. 154(b) by 0 days.

(21) Appl. No.: 15/508,935

(22) PCT Filed: Sep. 18, 2014

(86) PCT No.: PCT/IT2014/000249
§ 371 (c)(1),
(2) Date: Mar. 6, 2017

(87) PCT Pub. No.: WO2016/042582
PCT Pub. Date: Mar. 24, 2016

(65) Prior Publication Data
US 2017/0245968 A1 Aug. 31, 2017

(51) Int. Cl.
*A61C 11/00* (2006.01)
*A61C 11/08* (2006.01)

(52) U.S. Cl.
CPC .......... *A61C 11/001* (2013.01); *A61C 11/003* (2013.01); *A61C 11/087* (2013.01)

(58) Field of Classification Search
CPC ... A61C 11/001; A61C 11/003; A61C 11/006; A61C 11/08–088; A61C 19/04; A61C 19/045
USPC ...................................................... 433/53–68
See application file for complete search history.

(56) References Cited

U.S. PATENT DOCUMENTS

| 2,608,762 | A |   | 9/1952 | Fox |
| 4,391,589 | A | * | 7/1983 | Monfredo ............... A61C 11/02 433/55 |
| 5,281,135 | A | * | 1/1994 | Schwestka-Polly ... A61C 11/00 433/215 |
| 5,876,200 | A | * | 3/1999 | Tsubota ............... A61C 11/022 433/56 |

(Continued)

FOREIGN PATENT DOCUMENTS

DE 202004004955 U1 6/2004

OTHER PUBLICATIONS

International Search Report of PCT (EPO), dated Jun. 29, 2015.

*Primary Examiner* — Ralph A Lewis
(74) *Attorney, Agent, or Firm* — Patshegen IP LLC; Mosche Pinchas

(57) ABSTRACT

The Modular system for the realization of orthodontic Gipsoteca models with the faithful tilting of the individual occlusal plane and mobile and fixed prostheses and other orthodontic aids such as bites or splints, comprises a first module consisting of a supporting device (1) and additional aids, such as bases, muffles, little frames, curved and flat plates, a base for the transfer of static relationships between the dental arches, the individual face bow and the injection piston, suitable to make up, in combination with the device (1), additional modules. The present invention allows to facilitate different dental, processing techniques and reduce processing times and possible errors caused by the realization and the squaring of the artifact.

9 Claims, 14 Drawing Sheets

(56) References Cited

U.S. PATENT DOCUMENTS

| | | | | |
|---|---|---|---|---|
| 5,993,208 A * | 11/1999 | Jonjic | .................... | A61C 13/04 |
| | | | | 433/34 |
| 6,102,698 A * | 8/2000 | Staples | ................. | A61C 11/00 |
| | | | | 433/56 |
| 6,431,871 B1 * | 8/2002 | Luthardt | ............ | A61C 13/0004 |
| | | | | 433/223 |
| 8,021,149 B2 * | 9/2011 | Gutman | ................. | A61C 11/00 |
| | | | | 433/229 |
| 8,429,425 B2 * | 4/2013 | Ko | ...................... | G06F 11/1469 |
| | | | | 707/640 |
| 2007/0037115 A1 * | 2/2007 | Sim | ........................ | A61C 9/002 |
| | | | | 433/57 |
| 2007/0196782 A1 * | 8/2007 | Noguchi | .............. | A61C 11/001 |
| | | | | 433/56 |
| 2008/0187882 A1 * | 8/2008 | Margossian | ......... | A61C 19/045 |
| | | | | 433/68 |
| 2009/0325121 A1 * | 12/2009 | Ragade | ................ | A61C 11/022 |
| | | | | 433/57 |
| 2010/0143858 A1 * | 6/2010 | Okkerse | ............... | A61C 11/022 |
| | | | | 433/34 |
| 2012/0244490 A1 * | 9/2012 | Tamburrino | ......... | A61C 19/045 |
| | | | | 433/73 |

* cited by examiner

MODULAR SYSTEM FOR THE REALIZATION OF ORTHODONTIC GYPSUM MODELS

The present invention covers a system having interchangeable and coupled modules to a single supporting device, which allows to facilitate different dental, processing techniques and reduce processing times and possible errors caused by the realization and the squaring of the artifact.

Many essential aids are known to the dental technician so as to determine the prosthetic solution and the static relationships that exist between two dental arches: face bows, articulators, verticulators, model masters and others. For example, among the oldest patents, there are known U.S. Pat. No. 1,589,973 of J S Landa, dated 1925, which explains a device (facial bow) for the measurement of the occlusal plane; U.S. Pat. No. 1,733,507, dated 1927, of McCollum which describes a device (articulator) for the realization of dental prostheses; U.S. Pat. No. 2,545,249, dated 1948, of S. Ackerman which describes a device (verticulator) that enables the construction of orthodontic models. In recent years, evolved types of articulators have been marketed having average, semi-adaptable and adaptable values that let play, in an increasingly similar manner, the features of the mechanical anatomy of the masticatory system.

However, this technique misses a simple, fast and safe system for the construction of orthodontic Gipsoteca models with the tilting of the single occlusal plane and fixed and removable prosthesis and other dental aids, which consists of a basic module for adjusting the positioning of additional devices after carrying out the transfer of information obtained with the measuring device of the face bow, such as: transfer bases for the upper and lower arches, which are aligned so as to keep the articulation in all their positions and angles after their realization; a pair of muffles with their supports, for the realization of mobile dental prosthesis, with the resin system by injection; module for hot relining and realization of fixed prosthesis with the lost wax technique; various other aids for the realization of the Gipsoteca model, such as a little rigid frame which can be filled, through a hole, with liquid material through an injection piston and precreate the final shape of the prototype, a curved plate to position the model of the lower arch according to the curve of Spee, a straight grooved plate so as to center the arch model in the upper base; a small graduated pillar to determine the median height of the adjustable model with screws; a module for cold relining of dental prostheses with various aids: a curved plate to anchor the prosthesis onto the model, a straight plate to center the model to the base, the reference model, the mobile prosthesis to be relined, a little base for the model of the lower prosthesis; a vertical articulator with the positioning of the individual occlusal plane for the realization of gnathologic bites, split and orthodontic appliances. Therefore, the scope of the present invention is a modular system for orthodontic, Gipsoteca models which faithfully reproduces the tilting of the single occlusal plane and mobile and fixed prosthesis and other dental aids, able to reduce processing times and any errors caused by the realization and the squaring of the artifact, which involves the use of a positioning and adjustment device, particularly of the static relationships (occlusion) between the dental arches, and of different interchangeable modules depending on the type of work to be performed.

The scope and advantages and other features will be evident and further described by the following description and attached drawings, which are not limited and are provided for illustrative purposes only.

Figure 1:
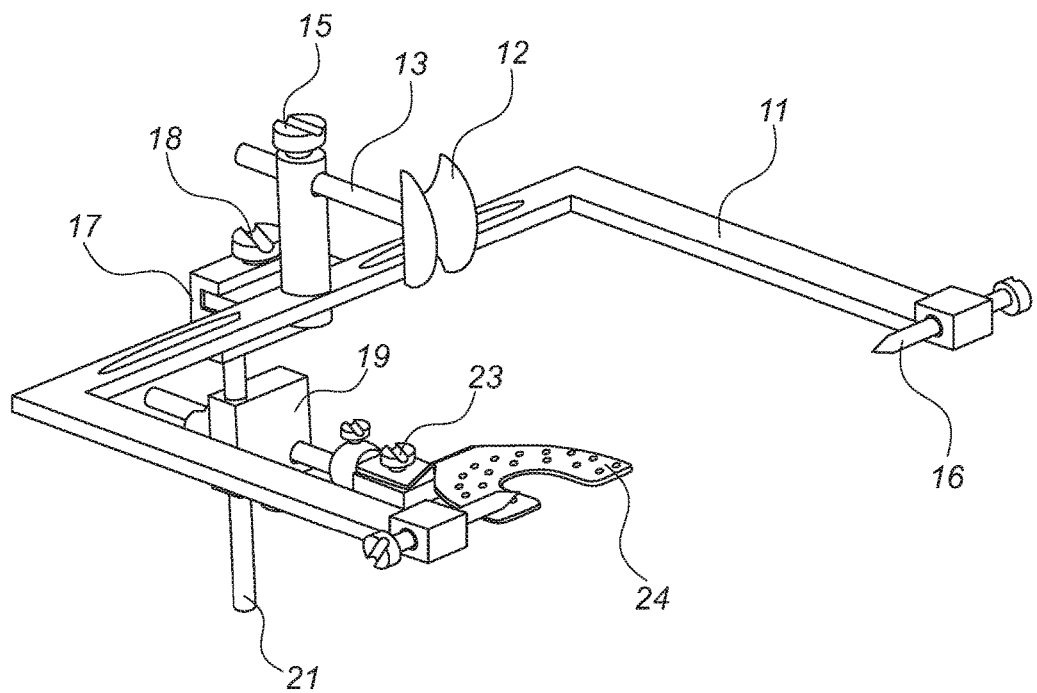
FIG. 1 shows, in a three-dimensional view, the device measuring the tilting of the occlusal plane.
Figure 2:
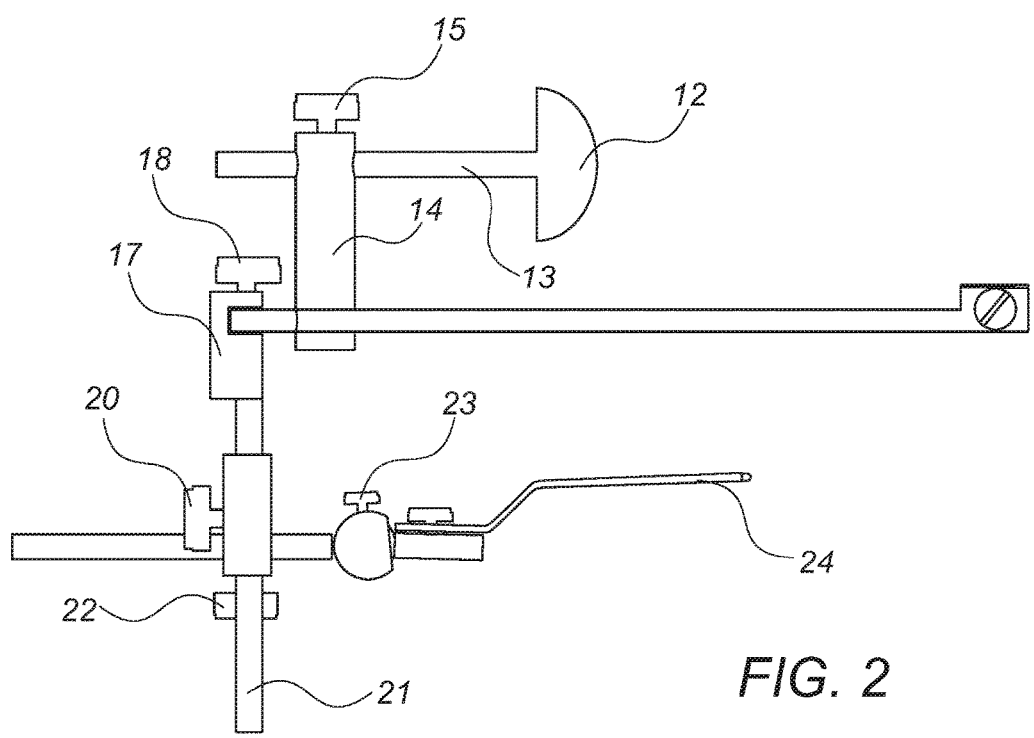
FIG. 2 shows, in a side view, the device measuring the tilting of the occlusal plane.
Figure 3:
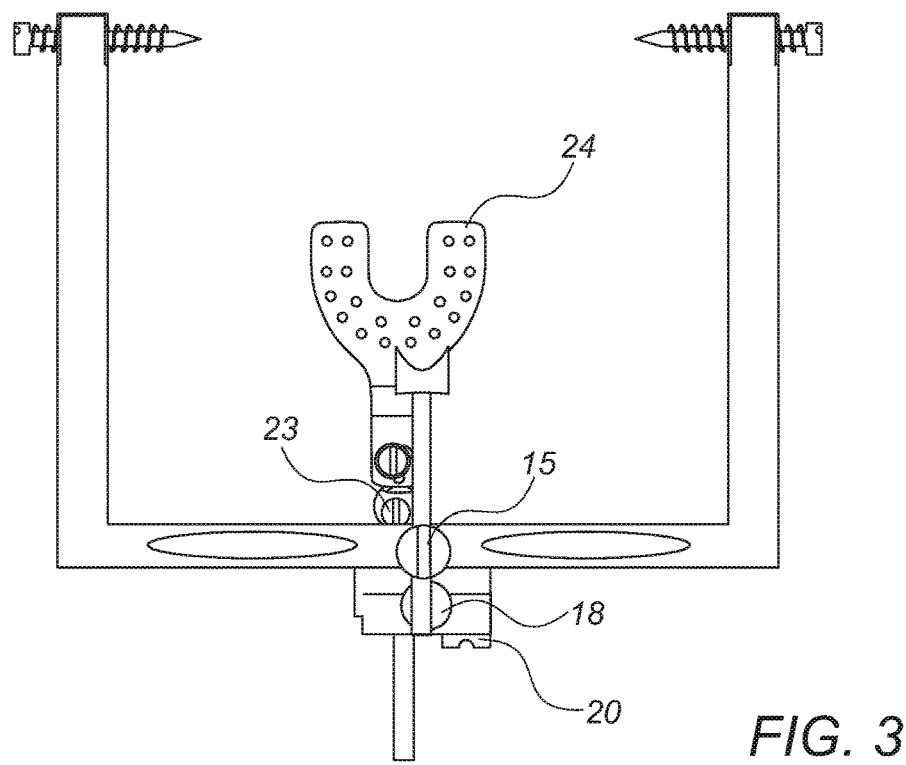
FIG. 3 shows, in a top plan view, the overall device measuring the tilting of the occlusal plane.
Figure 4:
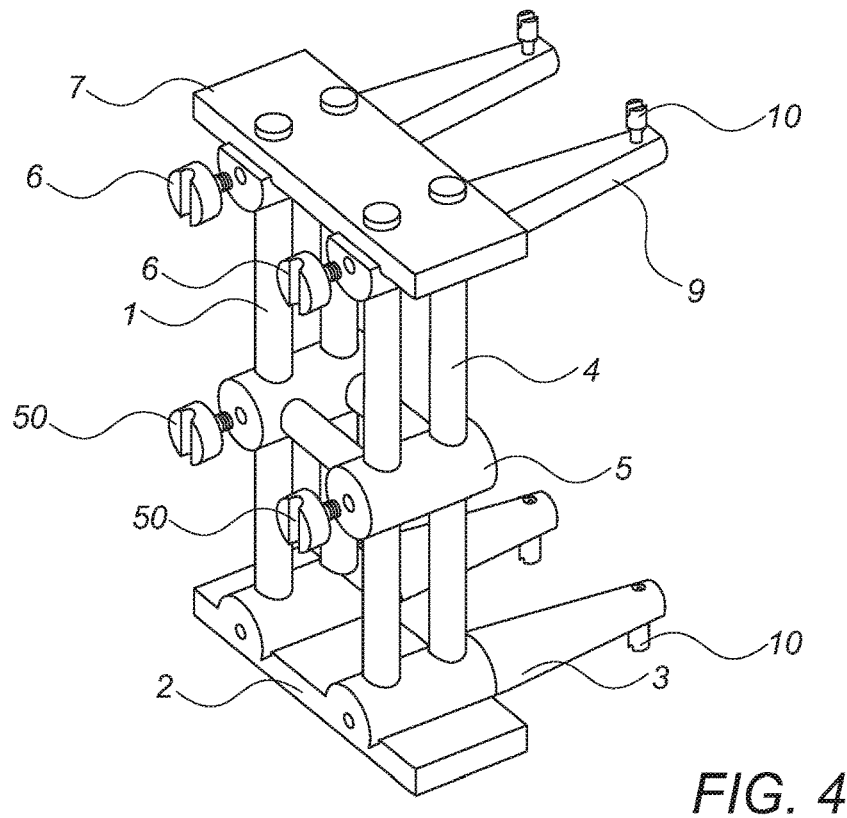
FIG. 4 shows, in a three-dimensional view, the overall supporting and adjustment device.
Figure 5:
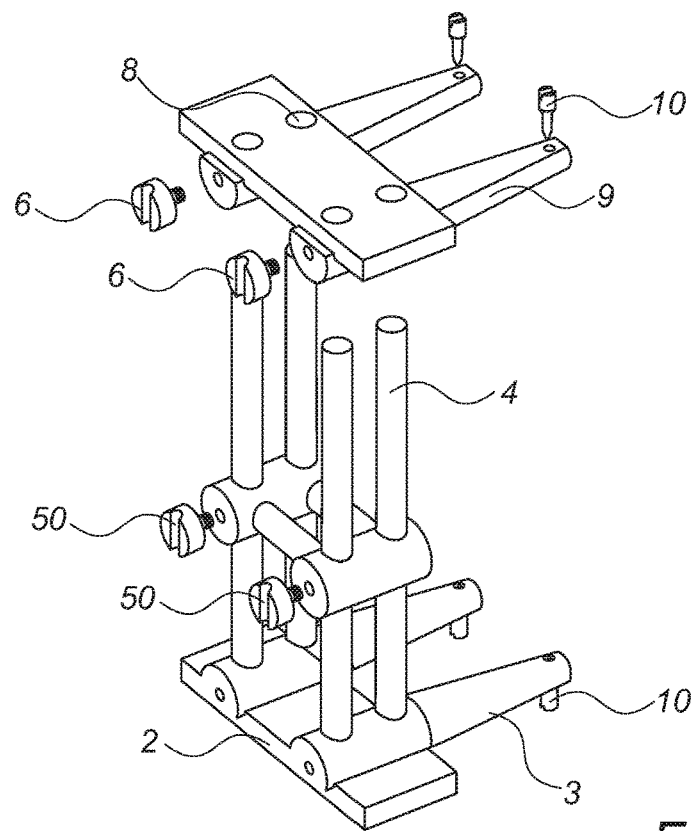
FIG. 5 shows, in a three-dimensional view, the overall supporting and adjustment device with the top part detached.
Figure 6:
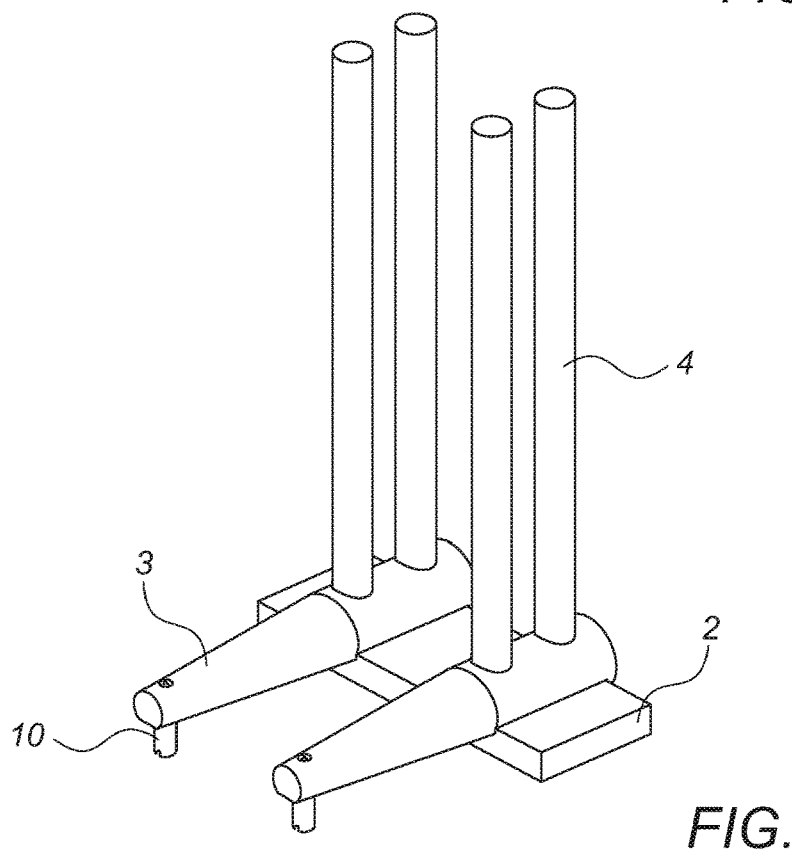
FIG. 6 shows, in a three-dimensional view, the supporting and adjustment device devoid of the upper and central part.
Figure 7:
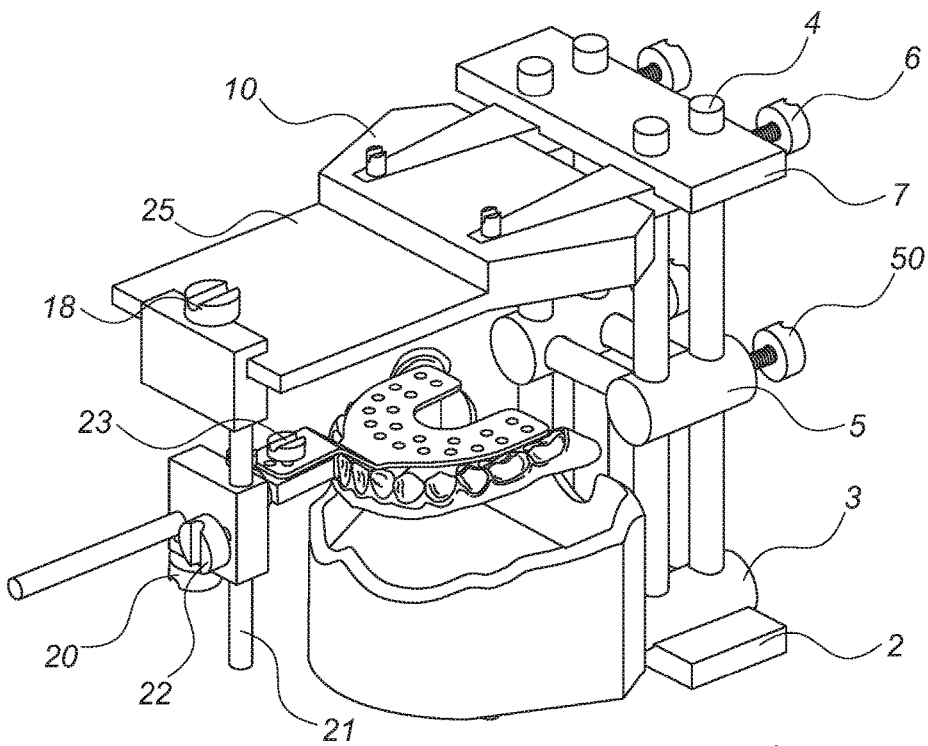
FIG. 7 shows, in a three-dimensional view, the overall transfer device of the measurement of the tilting of the occlusal plane on the supporting device.
Figure 8:
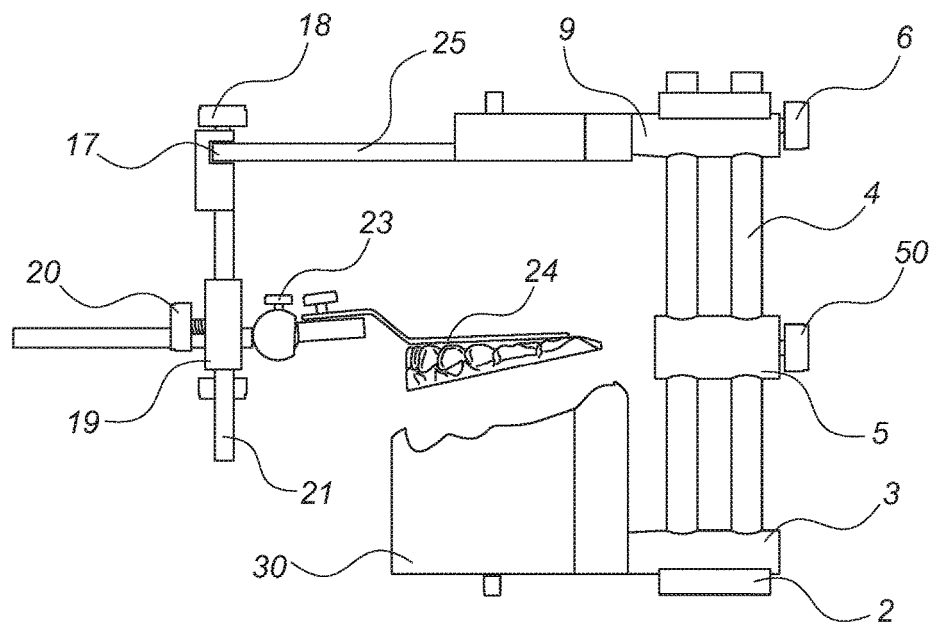
FIG. 8 shows, in a side view, the component elements for transferring the measurement of the tilting of the occlusal plane on the supporting device provided with a model of the lower arch.
Figure 9:
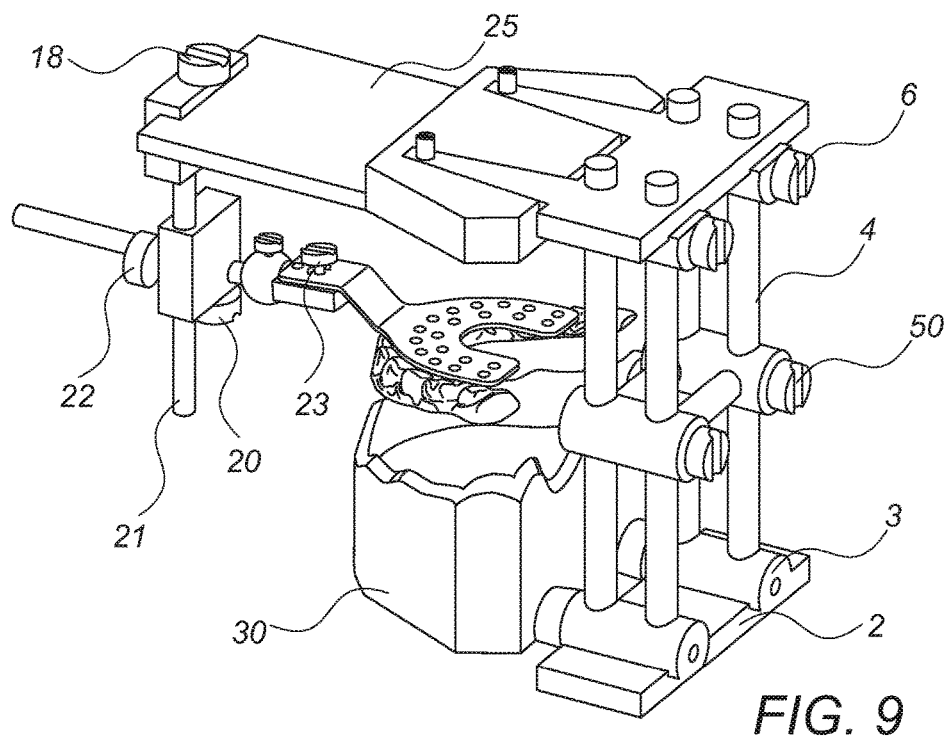
FIG. 9 shows, in a three-dimensional view, the component elements for transferring the measurement of the tilting of the occlusal plane on the supporting device provided with a model of the lower arch.
Figure 10:
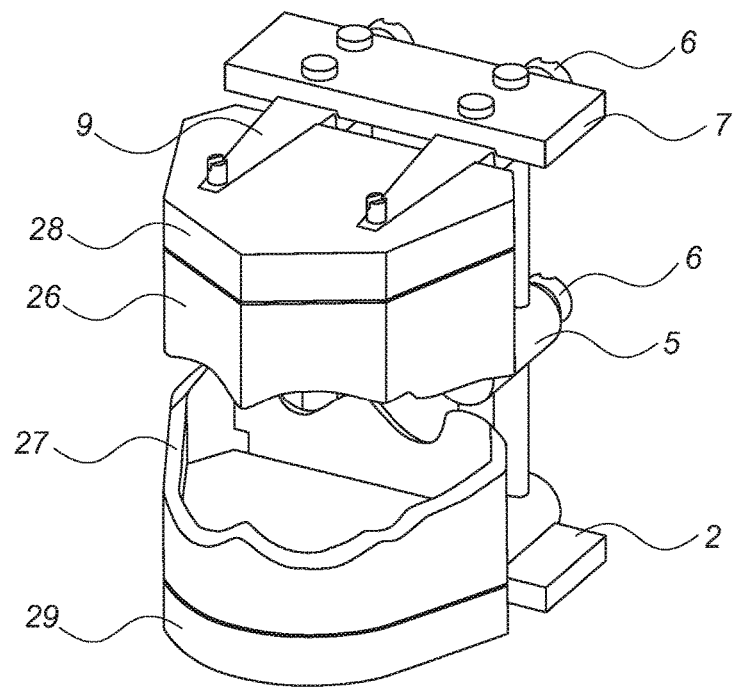
FIG. 10 shows, in a three-dimensional view, the supporting and adjustment device with a custom pair of lower and upper bases with the anchoring supports for the creation of dental arch models out of Gipsoteca plaster.
Figure 11:
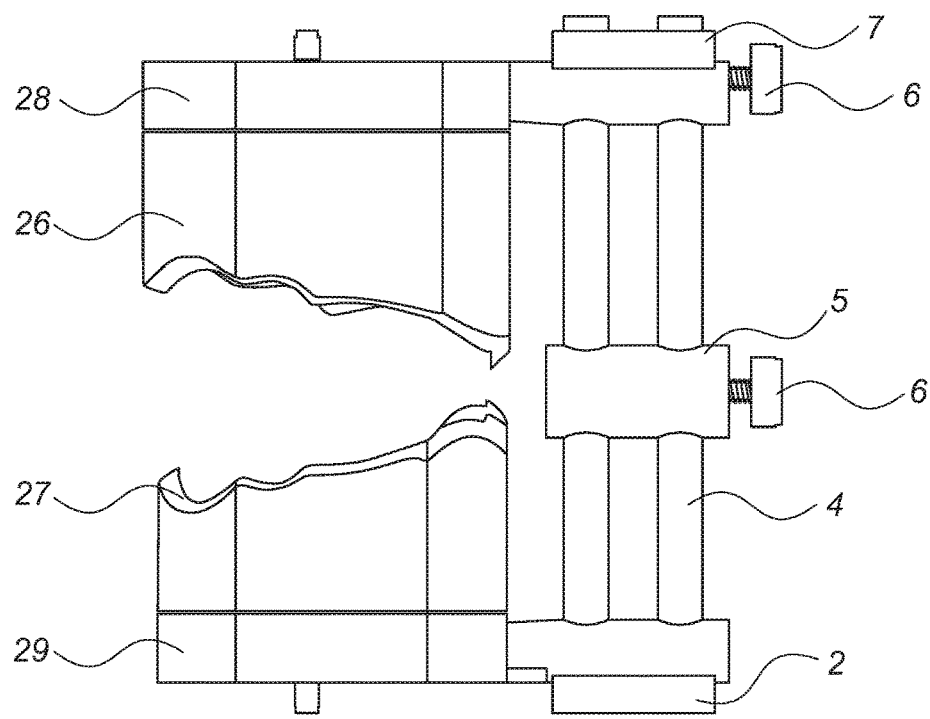
FIG. 11 shows a side view of the supporting and adjustment device with a pair of custom lower and upper bases with the anchoring supports.
Figure 12:
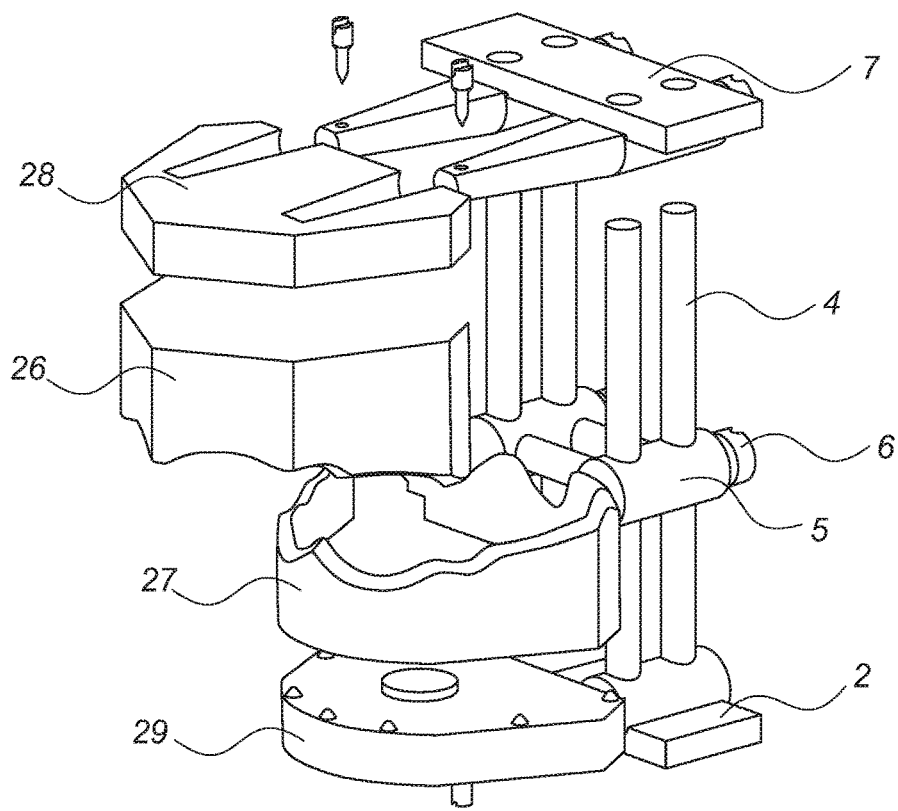
FIG. 12 shows a perspective view of the supporting and adjustment device with a pair of lower and upper custom bases with their disconnected anchoring supports.
Figure 13:
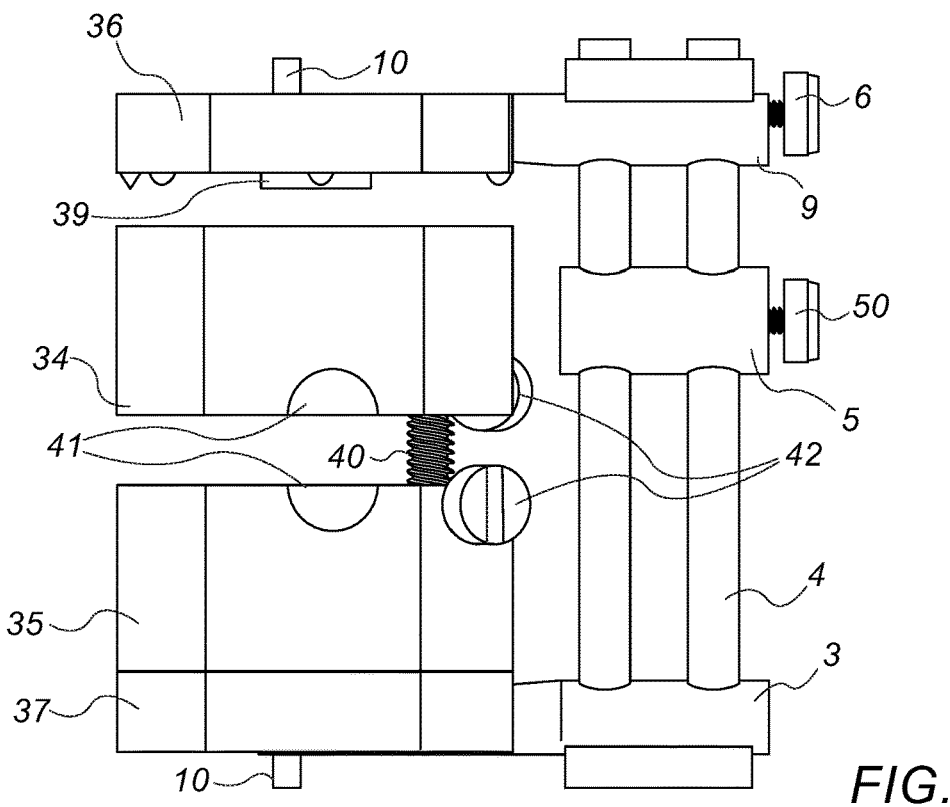
FIG. 13 shows a side view of the supporting and adjustment device with a pair of muffles for injections with their holders, for the realization of mobile dental prosthesis, with the resin system for injection, or of hot relining and the realization of fixed prosthesis with the lost wax technique.
Figure 14:
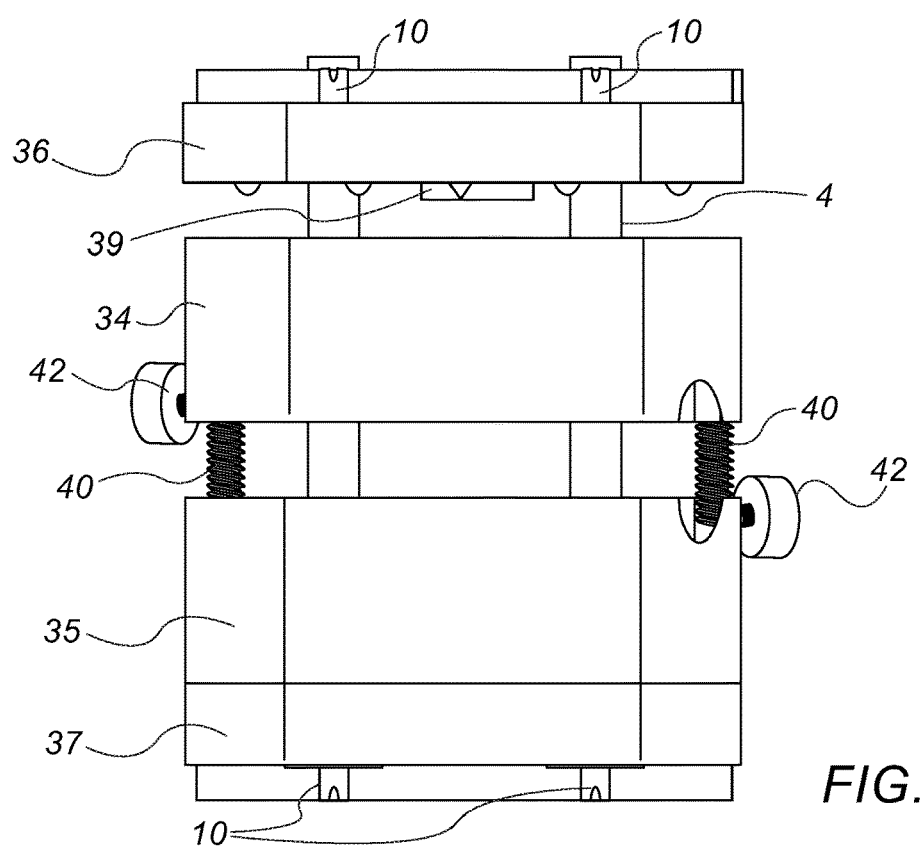
FIG. 14 shows a front view of the same supporting and adjustment device.
Figure 15:
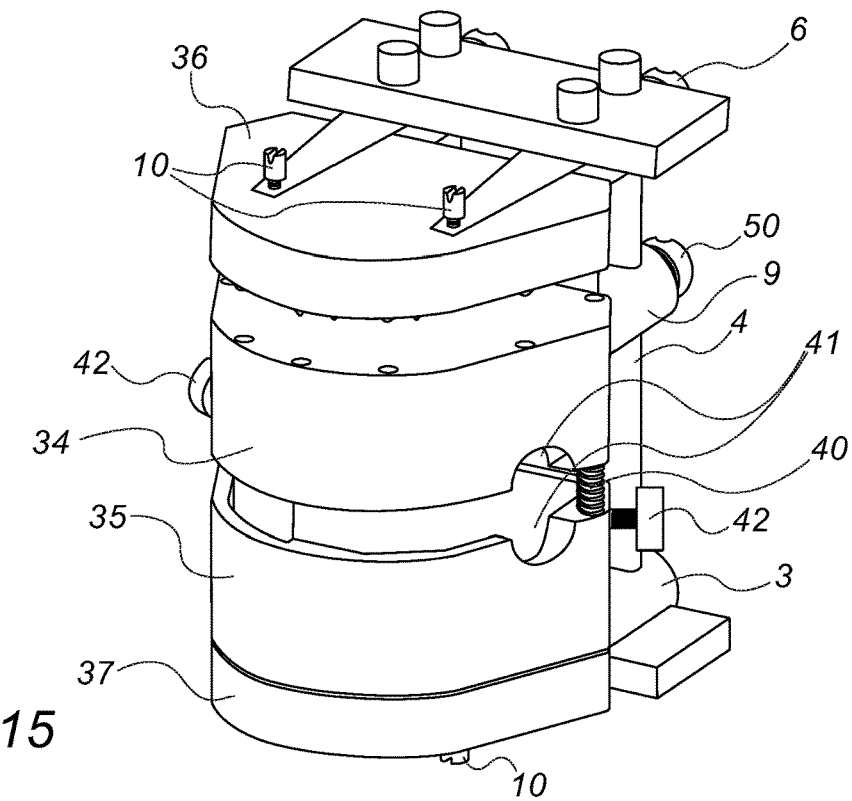
FIG. 15 shows a side view of the same supporting and adjustment device with the top muffle detached from the lower muffle.
Figure 16:
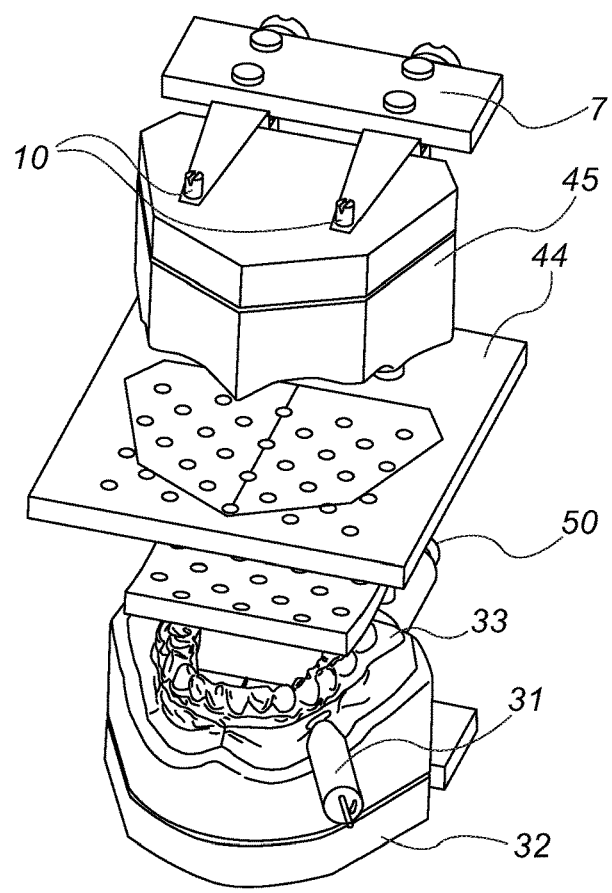
FIG. 16 shows a three-dimensional view of the supporting and adjustment device with various aids for the realization of the arch model.
Figure 17:
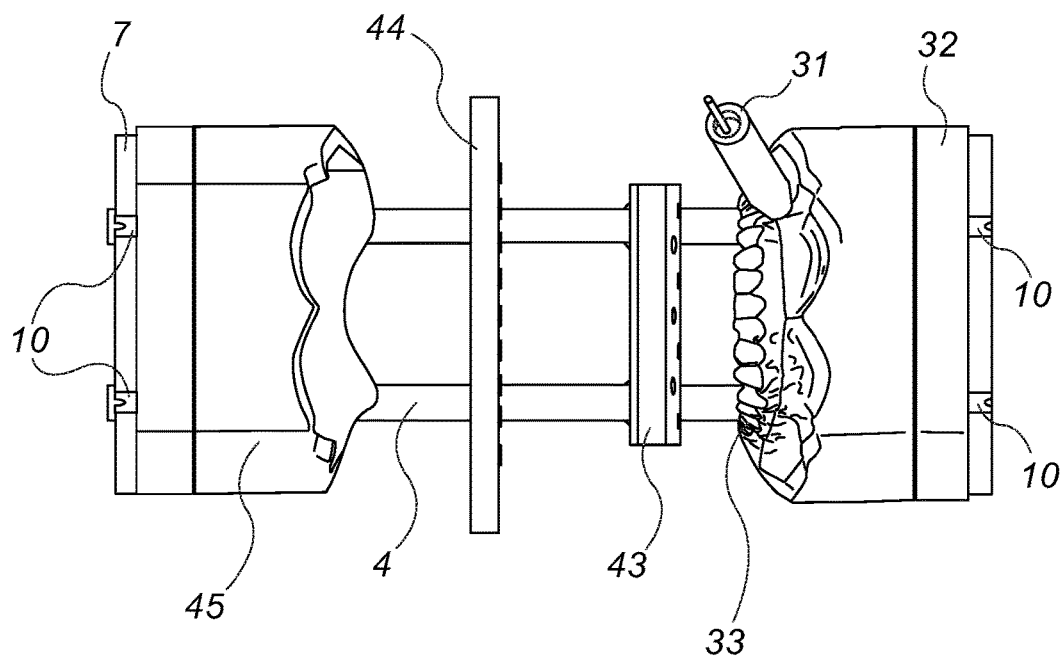
FIG. 17 shows a front view of the previous supporting and adjustment device.
Figure 18:
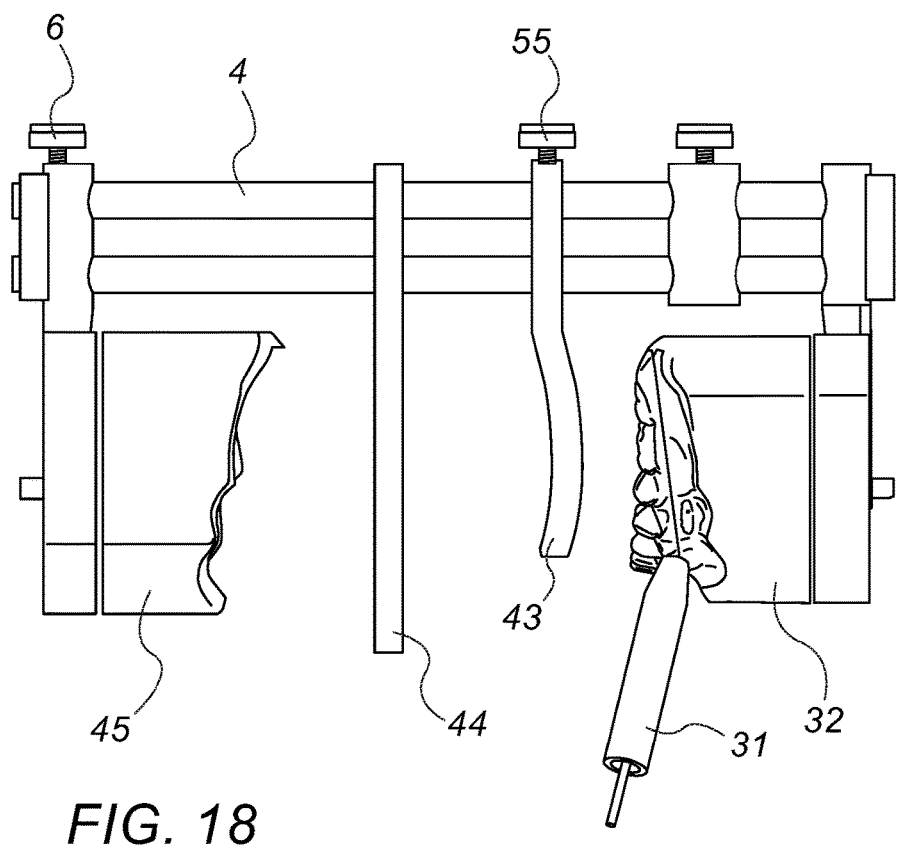
FIG. 18 shows a side view of the previous supporting and adjustment device.
Figure 19:
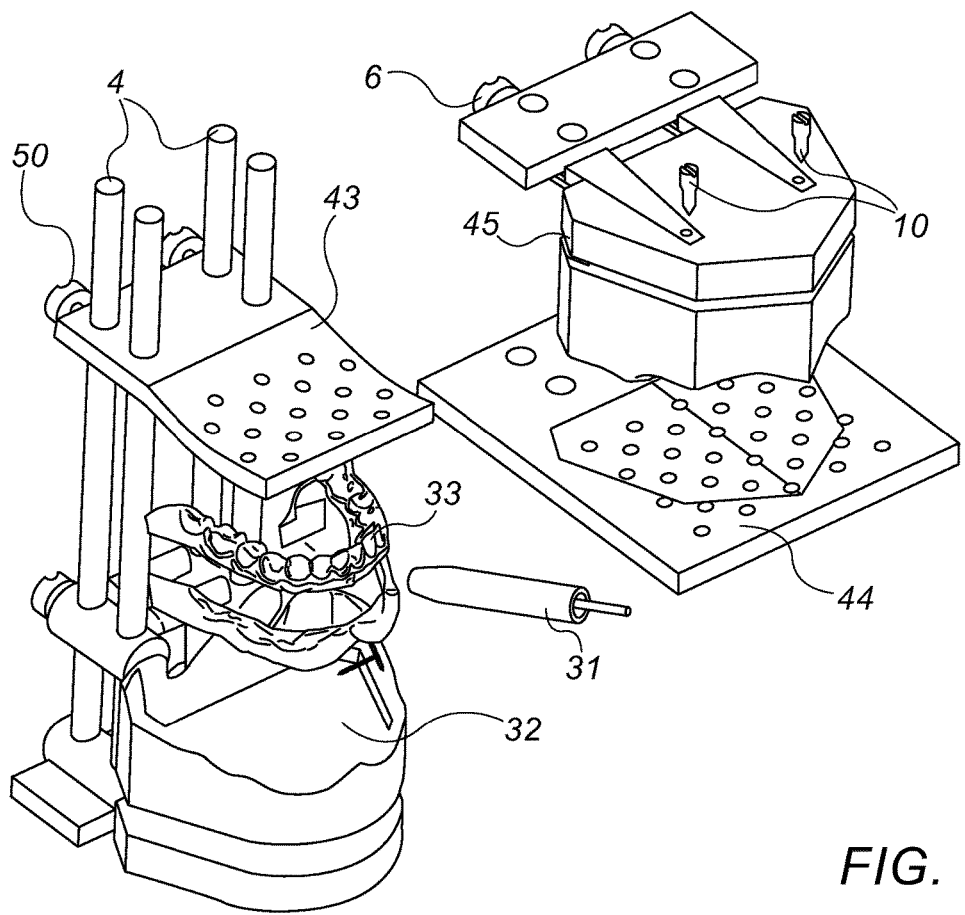
FIG. 19 shows a perspective view of the previous supporting and adjustment device.
Figure 20:
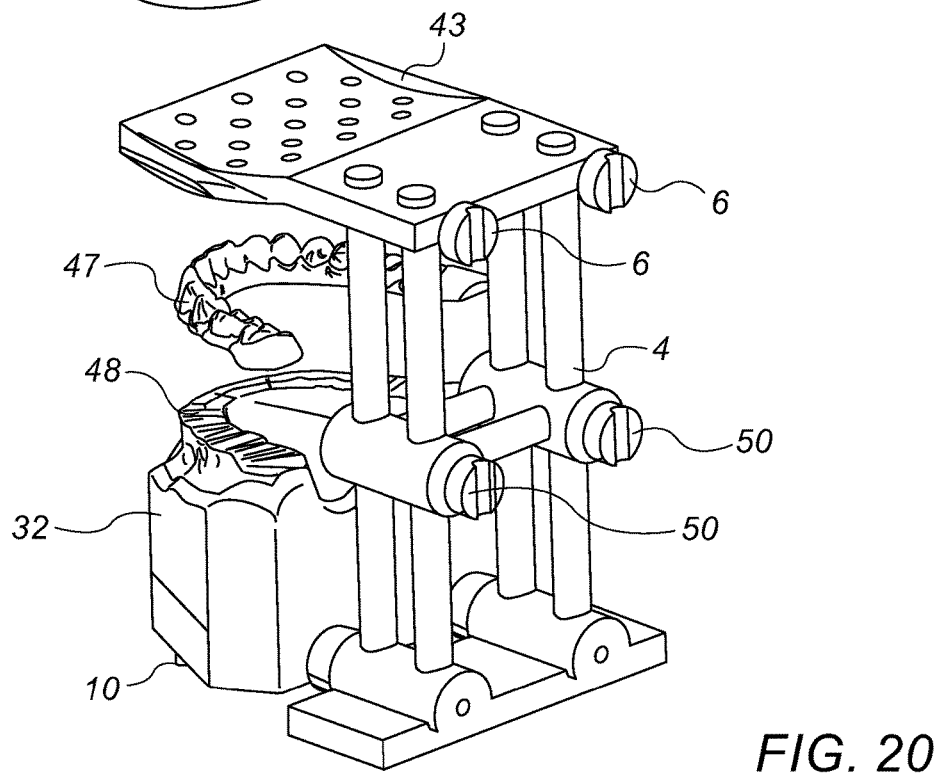
FIG. 20 shows a rear three-dimensional view of the device for cold relining of the dental prostheses.
Figure 21:
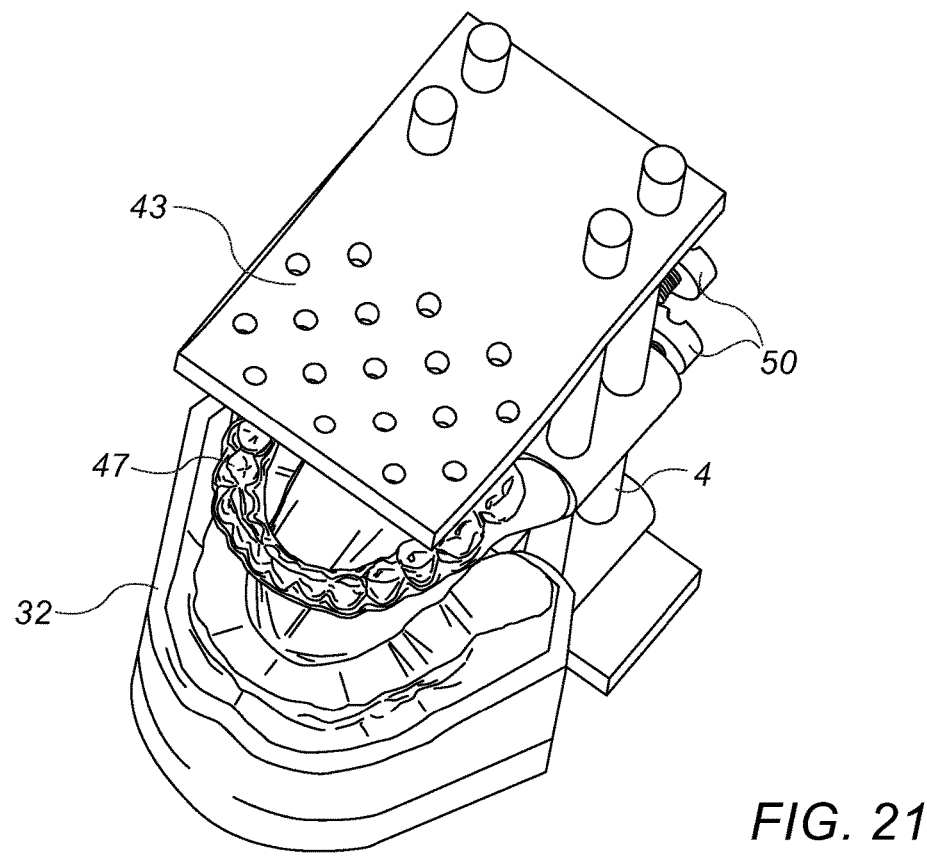
FIG. 21 shows a top three-dimensional view of the previous device.
Figure 22:
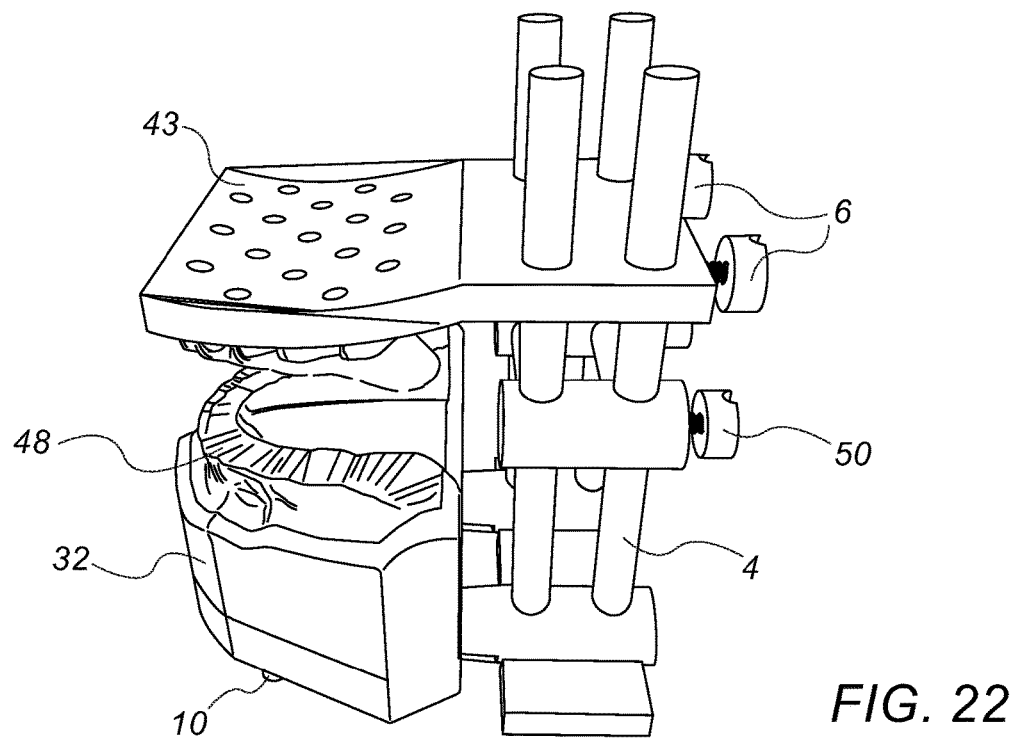
FIG. 22 shows a side three-dimensional view of the previous device during a processing stage.
Figure 23:
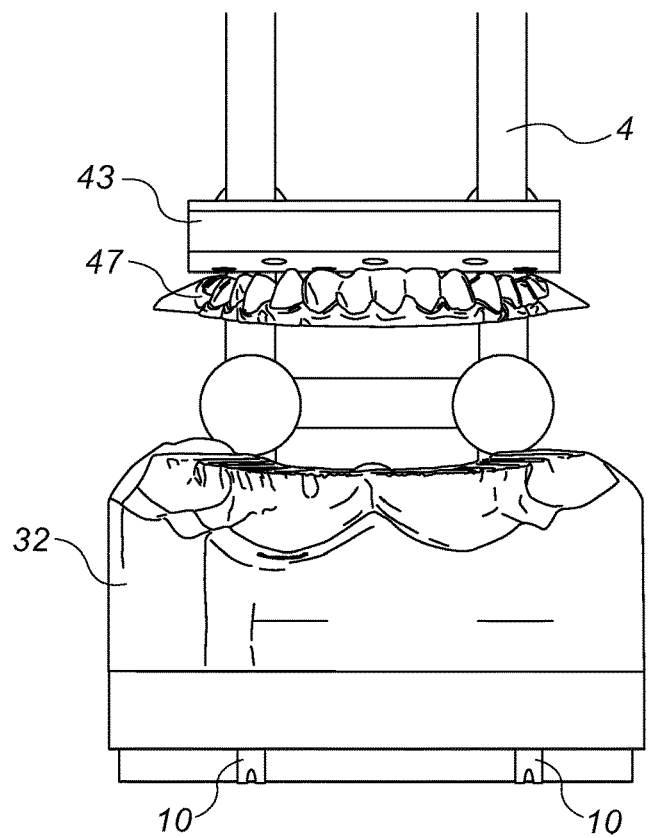
FIG. 23 shows another three-dimensional view of the previous device.
Figure 24:
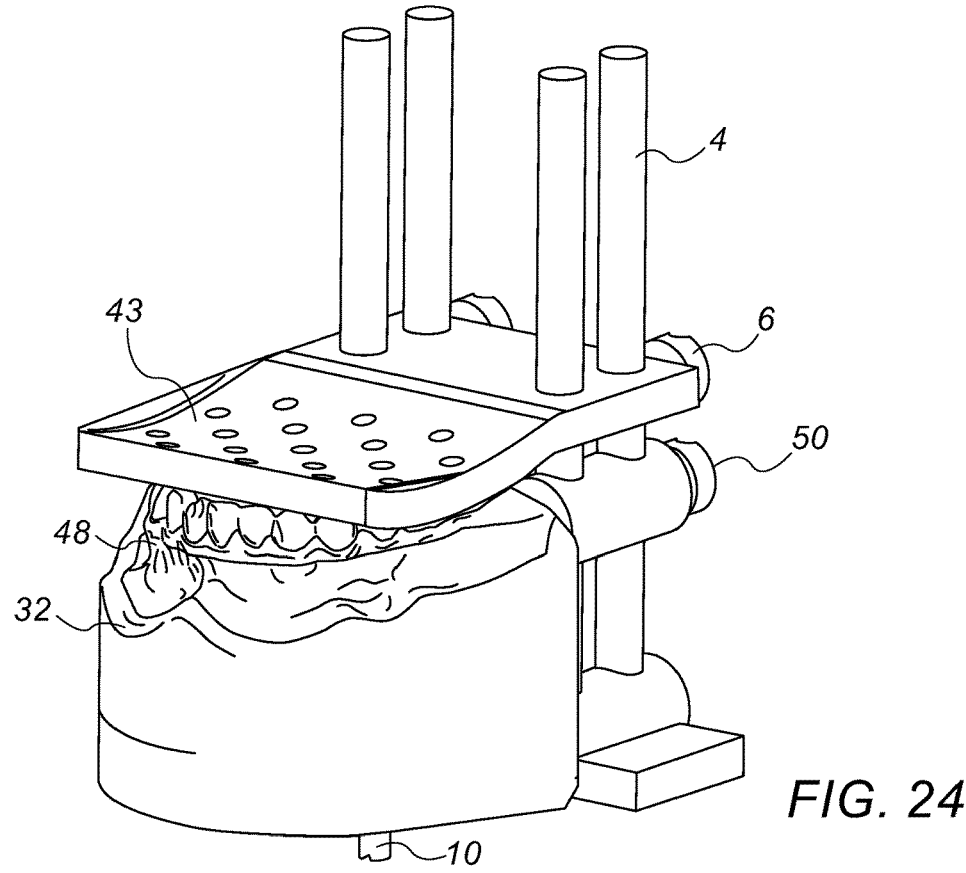
FIG. 24 shows, in a three-dimensional prospective view, a processing stage of the previous device.
Figure 25:
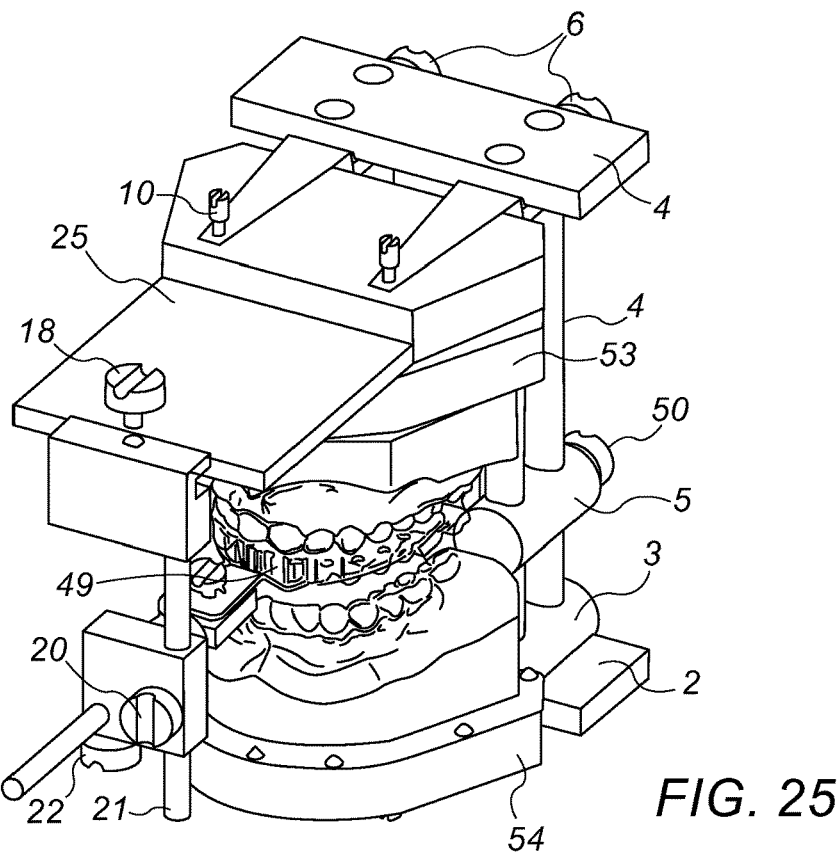
FIG. 25 shows a three-dimensional view of the vertical articulator for the realization of occlusal splints or bites and other orthodontic devices.
Figure 26:
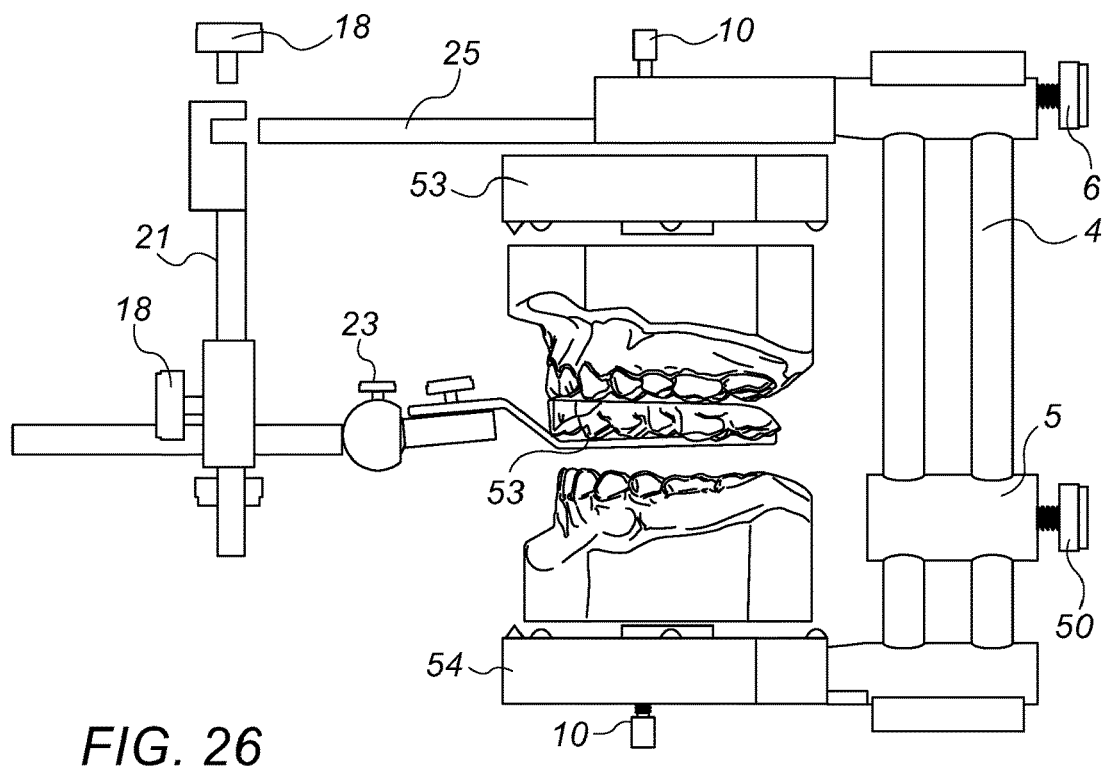
FIG. 26 shows a side view of the vertical articulator.
Figure 27:
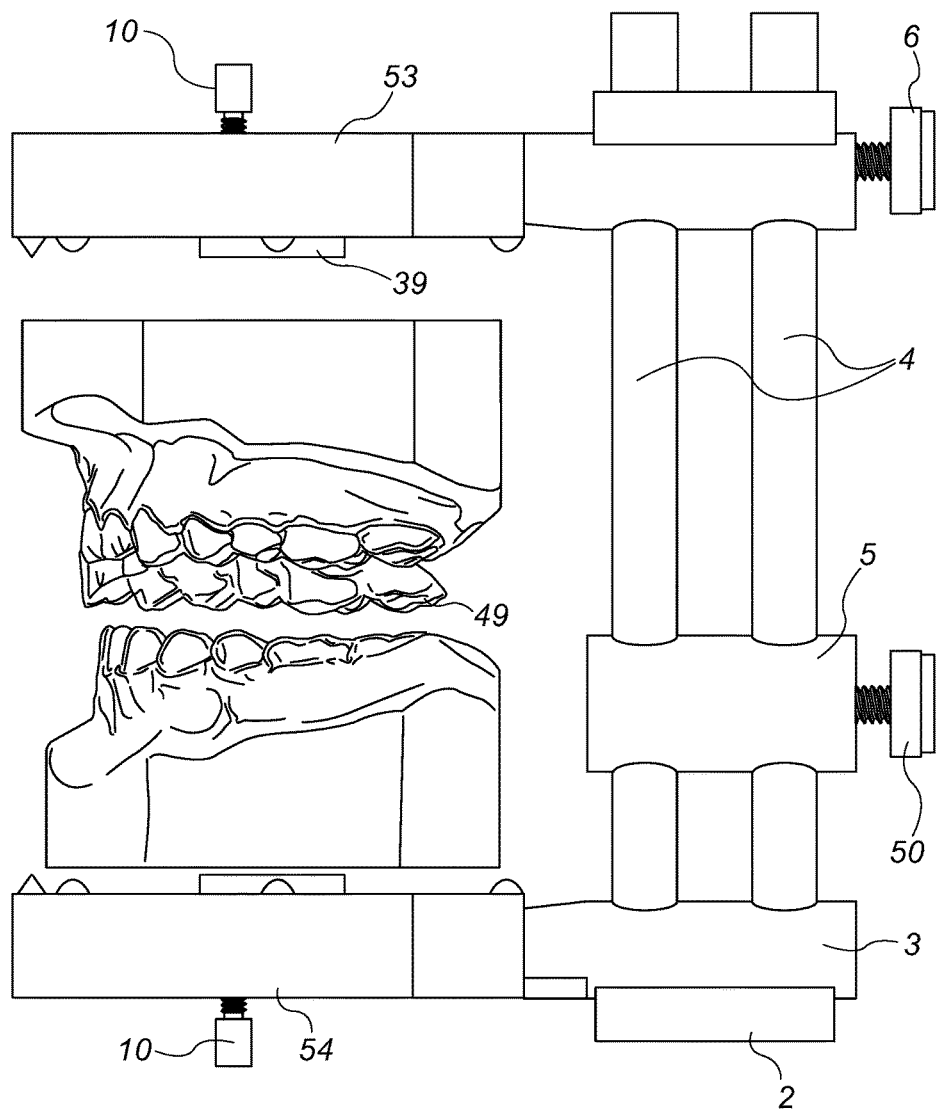
FIG. 27 shows a side view of the vertical articulator without the transfer module.

In accordance with the drawings, the modular system which allows to create orthodontic Gipsoteca models with different angles and, in accordance with international schools of reference, by highlighting the tilting of the individual occlusal plane, and fixed and mobile prosthesis and other dental aids, has, for the above-mentioned applications, a single supporting device which makes up the basic module for adjusting the positioning of additional devices, such as transfer bases, plates and supports or for models of upper and lower arches. Said supporting device (1) is made up of a metal frame comprising a rectangular plate (2), that acts as a lower base, to which are attached, transversely, two parallel, semi-cylindrical, cantilevered elements (3) having a conical run along their length; orthogonally, two pairs of cylinders having a circular section (4) are fixed, which are provided on their surface with a scale for measuring the height, on which scrolls an intermediate element having a shape of a quadrangular frame (5), whose position is fixed by threaded bolts (6); the topmost element of the frame (1) consists of a rectangular plate (7) with four holes (8), to which are attached transversely two cantilevered semi-cylindrical elements (9) which are placed parallelly and with a conical run along their length, whose position is secured by threaded bolts (6). The cantilevered semi-cylindrical elements (3) and (9) are provided, near their free ends, with anchoring screws (10).

The transfer of data, essentially the replicated tilting of the occlusal plane, onto the supporting device (1) takes place with the aid of a face bow (11). The individual face bow is made up of different components, in particular: a nasal plug (12) and its support (13), whose scrolling within the grooved plate (14) is governed and fixed by the threaded bolt (15); the positioning screws (16) of the face bow, the anchoring of the transfer (17) or other objects such as a little base (30) with the threaded fixing bolt (18); the support (19) which allows, through the threaded bolt (20), to adjust the height on the small graduated pillar (21), as well as the length and the orbit of the fork (24), always through bolts, respectively (22) and (23).

In particular, the information of the occlusal plane is transferred onto the supporting device (1) with the aid of a transfer base (25), which is suitably anchored onto the transfer module, via the threaded bolt (18).

In a first application of the present invention, the supporting device (1) is coupled with a custom pair of upper and lower bases (26, 27) with their anchoring supports, respectively (28, 29), for the creation of arch models out of Gipsoteca plaster casts: the pair of bases (26, 27), for the upper and lower arches are aligned so as to keep the articulation in all their positions and angles after their realization.

The correct positioning and alignment of the two arches is carried out in a controlled manner, by simply placing the two semi-arches above the plaster casting, with some centering bases.

Regarding the model of traditional Gipsoteca, the alignment of both arches occurs both sagittally and vertically, through flat or curved centering bases. The centering base on the support (1) can be stopped by tightening the threaded bolt (50).

The application includes 6 pairs of interchangeable bases to cope with the different sizes of the dental arches, and so that they can play all the different angles of the bases, required by the different international schools, by highlighting the tilting of the individual occlusal plane.

The inclusion of the plaster takes place through a piston (31) in a hole (32) located on a side end of the frame (33).

In a second application, the supporting device is coupled (1) with a pair of muffles (34, 35) for injections with their supports (36, 37), for the realization of mobile dental prosthesis, with the resin system for injection, or of hot relining and the realization of fixed prosthesis with the lost-wax technique; the muffles (34, 35) are provided with side holes (38), are anchored to the support bases (36, 37) with magnets (39) and guides with endless worms (40). On the side end of the muffles, a hole (41) is available through which the casting of the resin will flow to the sprue bushings. To avoid any occlusal increase, two muffles (34, 35) are hermetically sealed to each other using the endless worm (40) and are locked by a bolt (42). The kit for jetting the material will be made up of a tank, a vent valve and an outer piston (31) for the casting of the material after its mixing.

In a third application, the supporting device is coupled with (1) various aids for the realization of the arch model: a little rigid frame (33), which can be filled, through a hole (32), with liquid material by an injection piston (31) and pre-create the final shape of the prototype; a curved plate (43) to position the model of the lower arch according to the curve of Spee; a straight grooved plate (44) to center the model of the arch on the lower base (45); a small graduated pillar for determining the median height of the model, adjustable with the bolt (50).

In a fourth application, that is for the cold relining of the dental prostheses, various aids are coupled to the supporting device (1): the curved plate (43) to anchor the prosthesis on the model, the straight plate (44) to center the base model, the reference model (46), the dental prosthesis to be relined (47) and the base (48) for the model of the lower prosthesis.

After developing the model in the base socket, the prosthesis will be fixed to the plate (43) and degreased. The desired height of the prosthesis support (1) is fixed by the nut (50). Afterward, the prosthesis is put back on the previously developed model and the resin casting will be poured, so as to have the same height and avoid occlusal increases.

This significantly reduces the processing time, compared to traditional techniques.

In a fifth application for the realization of bites or occlusal splints and other orthodontic devices, the information of the occlusal plane is transferred onto the supporting device (1) which is used as a vertical articulator by positioning the splint (49) and the upper (51) and lower (52) processing models fixed on the device (1) respectively to the bases (53) and (54) by maintaining the tilting of the single occlusal plane, obtained through the transfer base (25) and the fork (24). One of the advantages of the present invention is that each component is designed and developed with a .stl file and is reproducible at any time by printing it through a normal 3D printer or through milling.

The invention claimed is:

1. Modular system for the realization of orthodontic Gypsum models with the faithful tilting of the individual occlusal plane and mobile and fixed prostheses and other orthodontic aids, the system includes a first module of a supporting device comprising:
   a lower base having a bottom rectangular plate, and two bottom cantilevered semi-cylindrical elements attached to said bottom rectangular plate such that said two bottom cantilevered semi-cylindrical elements extended in parallel to one another, each one of said two bottom cantilevered semi-cylindrical elements includes a conical shape defined along the length thereof;

two pairs of cylindrical bars are orthogonally attached to said bottom rectangular plate, each cylindrical bar having a circular section and is provided on a surface thereof with a scale for measuring the height;

a quadrangular intermediate element affixed to said cylindrical bars by threaded bolts;

a topmost element having a top rectangular plate coupled to the top of said cylindrical bars, said top rectangular plate includes four holes for coupling to said two pairs of cylindrical bars said topmost element further includes two top cantilevered semi-cylindrical elements transversely attached to said top rectangular plate, such that said two top cantilevered semi-cylindrical extended in parallel to one another, each one of said top cantilevered semi-cylindrical elements includes a conical shape defined along the length thereof;

wherein position of said top semi-cylindrical elements is secured by threaded bolts and said top cantilevered semi-cylindrical elements and are provided, near their free ends, with anchoring screws for coupling to said top semi-cylindrical elements additional modules.

2. Modular system for the realization of orthodontic Gypsum models with the faithful tilting of the individual occlusal plane in claim 1 wherein the module is made up by the supporting device and by a custom pair of upper and lower bases with their anchoring supports, aligned sagittally and fastened vertically with the clamping bolt, with the placement of two half arches over the casting of plaster in a hole located on a end side of the frame, which takes place by induction through the piston.

3. Modular system for the realization of orthodontic Gypsum models with the faithful tilting of the individual occlusal plane, in claim 1, wherein six pairs of interchangeable bases are used for different sizes and angles of the dental arches.

4. Modular system for the realization of orthodontic Gypsum models with the faithful tilting of the individual occlusal plane and mobile and fixed prostheses, in claim 1 wherein the supporting device is coupled with a pair of muffles for injections, provided with side holes, and anchored to the supporting bases with magnets and guides with endless worms for the hermetic sealing between them, and blocked by a bolt; on the lateral end of the muffles a hole is provided for the casting of the resin in the sprue bushings.

5. Modular system in claim 1 wherein in the realization of mobile and fixed prostheses the supporting device is coupled with a: a rigid little frame, which, through a hole, is filled with liquid material by means of an injection piston and create the final shape of the prototype; a curved plate, for placement of the lower arch model according to the curve of Spee; a straight perforated plate to center the arch model in the upper base; a small graduated pillar for determining the median height of the model, adjustable with a bolt.

6. Modular system in claim 1 wherein in the realization of mobile and fixed prostheses the device for cold relining of the dental prosthesis is made up by coupling the supporting device with the curved plate to anchor the prosthesis onto the model, the straight plate for centering the model to the base, the base for the model of the lower prosthesis.

7. Modular system in claim 1 wherein in the realization of mobile and fixed prostheses, various aids are coupled to the bracket: the curved plate to anchor the prosthesis onto the model, the straight plate for centering the model to the base, the reference model and the base to the model of the lower prosthesis; the desired height of the prosthesis on the support is fixed by the nut.

8. Modular system in claim 1 wherein for the realization of bites or splints, the device is used as a vertical articulator by positioning the splint and the upper and lower processing modules are locked onto the device respectively to the bases and by keeping the tilting of the individual occlusal plane, obtained through the transfer base and the fork.

9. The modular system according to claim 1 wherein said additional modules are selected from a group consisting of: bases, muffles, frames, curved and flat plates, a base for the transfer of static relationships between dental arches, individual face bow and injection piston.

* * * * *